United States Patent
Ruthramoorthy et al.

(10) Patent No.: US 9,032,380 B1
(45) Date of Patent: May 12, 2015

(54) IDENTIFYING FUNCTION CALLS AND OBJECT METHOD CALLS

(71) Applicant: The MathWorks, Inc., Natick, MA (US)

(72) Inventors: Navaneetha K. Ruthramoorthy, Natick, MA (US); Kiran K. Kintali, Ashland, MA (US)

(73) Assignee: The MathWorks, Inc., Natick, MA (US)

( * ) Notice: Subject to any disclaimer, the term of this patent is extended or adjusted under 35 U.S.C. 154(b) by 204 days.

(21) Appl. No.: 13/693,439

(22) Filed: Dec. 4, 2012

Related U.S. Application Data

(60) Provisional application No. 61/566,940, filed on Dec. 5, 2011.

(51) Int. Cl.
*G06F 9/45* (2006.01)

(52) U.S. Cl.
CPC ..................................... *G06F 8/443* (2013.01)

(58) Field of Classification Search
None
See application file for complete search history.

(56) References Cited

U.S. PATENT DOCUMENTS

| | | | | |
|---|---|---|---|---|
| 7,900,193 B1* | 3/2011 | Kolawa et al. | ................ | 717/126 |
| 7,949,502 B2* | 5/2011 | Shakeri et al. | ................ | 703/6 |
| 8,046,751 B1* | 10/2011 | Avadhanula et al. | ........ | 717/156 |
| 8,180,964 B1* | 5/2012 | Koh et al. | ...................... | 711/118 |
| 8,234,105 B1* | 7/2012 | Aldrich et al. | ................. | 703/22 |
| 8,234,637 B2* | 7/2012 | Ghosh-Roy et al. | .......... | 717/155 |
| 8,352,505 B1* | 1/2013 | Venkataramani et al. | .... | 707/802 |
| 8,364,456 B2* | 1/2013 | Raghavan et al. | .............. | 703/13 |
| 8,402,449 B1* | 3/2013 | Biswas et al. | ................. | 717/146 |
| 8,418,158 B1* | 4/2013 | Koh et al. | ...................... | 717/151 |
| 8,468,510 B1* | 6/2013 | Sundararajan et al. | ....... | 717/152 |
| 8,473,901 B1* | 6/2013 | Johnson | ........................ | 717/110 |
| 8,549,470 B2* | 10/2013 | Ciolfi et al. | .................... | 717/105 |
| 8,739,129 B1* | 5/2014 | Mosterman et al. | .......... | 717/125 |
| 8,843,906 B1* | 9/2014 | Clark et al. | .................... | 717/143 |
| 8,856,766 B2* | 10/2014 | Frenkiel et al. | ................ | 717/156 |
| 2004/0088691 A1* | 5/2004 | Hammes et al. | ............... | 717/158 |
| 2006/0041872 A1* | 2/2006 | Poznanovic et al. | ........... | 717/140 |
| 2007/0168902 A1* | 7/2007 | Ogawa et al. | ................... | 716/18 |
| 2008/0127057 A1* | 5/2008 | Costa et al. | .................... | 717/106 |
| 2009/0019416 A1* | 1/2009 | Chugh et al. | ..................... | 716/18 |
| 2009/0044171 A1* | 2/2009 | Avadhanula | ................... | 717/105 |
| 2009/0044179 A1* | 2/2009 | Luszczek et al. | .............. | 717/149 |
| 2009/0077536 A1* | 3/2009 | Foti | ................................ | 717/116 |
| 2009/0179921 A1* | 7/2009 | Raghavan et al. | ............. | 345/689 |
| 2012/0036519 A1* | 2/2012 | Webb et al. | .................... | 719/328 |
| 2013/0159964 A1* | 6/2013 | Szpak | ............................ | 717/105 |
| 2013/0290928 A1* | 10/2013 | Johnson | ........................ | 717/109 |

* cited by examiner

*Primary Examiner* — Don Wong
*Assistant Examiner* — Roberto E Luna
(74) *Attorney, Agent, or Firm* — Harrity & Harrity, LLP

(57) ABSTRACT

A device receives program code, generated via a technical computing environment (TCE) and including code that requires further processing to execute, and identifies one or more function calls or one or more object method calls in the program code. The device creates a control flow graph, for the program code, based on the one or more function calls or the one or more object method calls. The device transforms the control flow graph into a data flow graph. The data flow graph includes a representation for each of the one or more function calls or the one or more object method calls. The device generates hardware code based on the data flow graph, the hardware code including code that does not require further processing to execute.

20 Claims, 12 Drawing Sheets

IDENTIFYING FUNCTION CALLS AND OBJECT METHOD CALLS

RELATED APPLICATION

This application claims priority under 35 U.S.C. §119 based on U.S. Provisional Patent Application No. 61/566,910, filed Dec. 5, 2011, the disclosure of which is incorporated by reference herein in its entirety.

BRIEF DESCRIPTION OF THE DRAWINGS

The accompanying drawings, which are incorporated in and constitute a part of this specification, illustrate one or more implementations and, together with the description, explain these implementations. In the drawings.

DETAILED DESCRIPTION

The following detailed description refers to the accompanying drawings. The same reference numbers in different drawings may identify the same or similar elements.

A technical computing environment (TCE) may provide a computing environment that allows users to perform tasks related to disciplines, such as, but not limited to, mathematics, science, engineering, medicine, business, etc., more efficiently than if the tasks were performed in another type of computing environment, such as an environment that required the user to develop code in a conventional programming language, such as C++, C, Fortran, Pascal, etc. In one example, a TCE may include a dynamically-typed programming language (e.g., the M language, a MATLAB® language, a MATLAB-compatible language, a MATLAB-like language, etc.) that can be used to express problems and/or solutions in mathematical notations.

Code generated by the TCE may include function calls and/or object method calls. A function call may include a function name followed by one or more arguments. One or more output values may be assigned as an output of the function call. A method may define behavior of an object. An object method may be called using function syntax that passes the object as a first (i.e., left-most) argument. However, it is difficult to identify function calls and object method calls in TCE designs targeted for hardware code generation.

Overview

Systems and/or methods described herein may identify function calls and/or object method calls in TCE designs targeted for hardware code generation. In one example, the systems and/or methods may receive code generated by a TCE, and may identify function call(s) and/or object method call(s) in the code. The systems and/or methods may create a control flow graph, for the code, based on the identified function call(s) and/or object method call(s). The control flow graph may preserve the hierarchy of the identified function call(s) and/or object method call(s). The systems and/or methods may transform the control flow graph into a data flow graph, and may generate hardware code based on the data flow graph. The data flow graph may be analyzed to determine opportunities for numeric and latency optimization in the code. Such opportunities may be implemented in the hardware code.

In one example, the code may be optimized so that performance associated with the code is improved along some parameter (e.g., power, area, latency, etc.). The optimized code may not necessarily mean that an optimum (e.g., no further improvements are possible) is attained.

Figure 1:
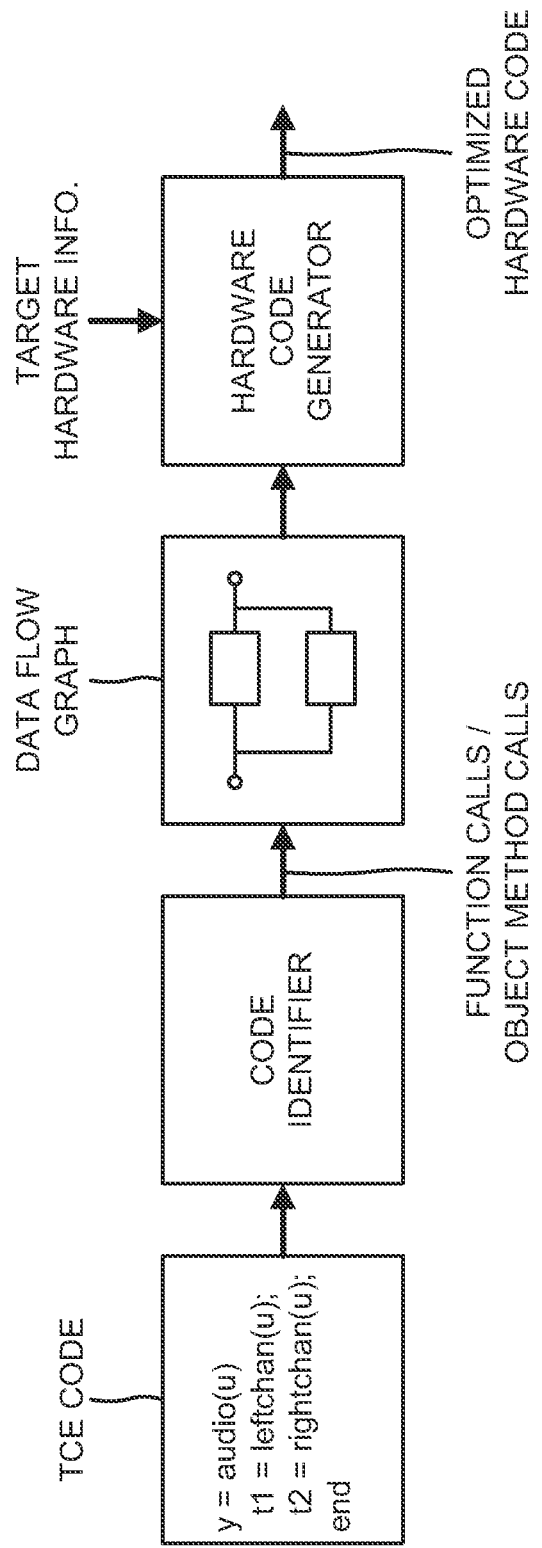
FIG. 1 is a diagram of an overview of an example implementation described herein.

FIG. 1 is a diagram of an overview of an example implementation described herein. As shown in FIG. 1, a computing environment, such as a technical computing environment (TCE), may include a code identifier component and a hardware code generator component. The code identifier component may receive code generated by the TCE, and may identify function calls and/or object method calls in the TCE code. The hardware code generator component may receive a data flow graph, for the TCE code, and may generate hardware code based on the data flow graph.

As further shown in FIG. 1, the code identifier component may receive code generated by the TCE. The TCE code may include text-based code that may require further processing to execute, binary code that may be executed, text files that may be executed in conjunction with other executables, etc. In one example, the TCE code may include the following syntax:

```
y = audio-equalizer (u);
    t1 = leftchannel-processing(u);
    t2 = rightchannel-processing(u);
    if (t1 > t2)
        y = t1;
    else
        y = t2;
    end
end.
```

The code identifier component may identify one or more function calls and/or object method calls in the TCE code. In one example, the code identifier component may use data types, sizes, complexity, etc. information associated with the TCE code to infer or identify a hierarchy of function calls and/or object method calls in the TCE code. The code identifier component may create a control flow graph, for the code, based on the identified function calls and/or object method calls. The control flow graph may preserve the hierarchy of the identified function call(s) and/or object method call(s). The code identifier component may transform the control flow graph into a data flow graph. The data flow graph may include nodes and/or signals provided between the nodes. The nodes may include representations of the function calls and/or object method calls that are to be executed by one or more hardware devices (e.g., a central processing unit (CPU), a graphical processing unit (GPU), etc.) of an architecture model. The signals may include representations of connections (e.g., communication interfaces and/or channels) provided between the function calls and/or object method calls. The code identifier component may provide the data flow graph to the hardware code generator component.

The hardware code generator component may receive the data flow graph, and may receive target hardware information. The target hardware information may include information associated with hardware devices (e.g., of the architecture model) upon which the TCE code is to be executed. The hardware code generator component may generate optimized hardware code based on the data flow graph and the target hardware information. In one example, the hardware code may be optimized by enabling the function calls and/or the object method calls to be executed in parallel and/or to share the hardware devices during execution. The optimized hardware code may be executed by the hardware devices associated with the target hardware information.

The terms "code" and "program code," as used herein, are to be used interchangeably and are to be broadly interpreted to include text-based code that may require further processing to execute; binary code that may be executed (e.g., executable files that may directly be executed by an operating system, bitstream files that can be used to configure a field programmable gate array (FPGA), Java byte code, object files combined together with linker directives, source code, makefiles, etc.); text files that may be executed in conjunction with other executables (e.g., Python text files, a collection of dynamic-link library (DLL) files with text-based combining, configuration information that connects pre-compiled modules, an extensible markup language (XML) file describing module linkage, etc.); etc. In one example, code may include different combinations of the above-identified classes (e.g., text-based code, binary code, text files, etc.). Alternatively, or additionally, code may include a dynamically-typed programming language (e.g., the M language, a MATLAB® language, a MATLAB-compatible language, a MATLAB-like language, etc.) that can be used to express problems and/or solutions in mathematical notations. Alternatively, or additionally, code may be of any type, such as function, script, object, etc., and a portion of code may include one or more characters, lines, etc. of the code. The code may be untimed in addition to being array-based and dynamically types.

The term "hardware code," as used herein, is to be broadly interpreted to include text-based code that may not require further processing to execute, such as, for example, C++ code, Hardware Description Language (HDL) code, very-high-speed integrated circuits (VHSIC) HDL(VHDL) code, Verilog, Java, and/or other types of hardware or software based code that may be compiled and/or synthesized.

Example Environment Arrangement

Figure 2:
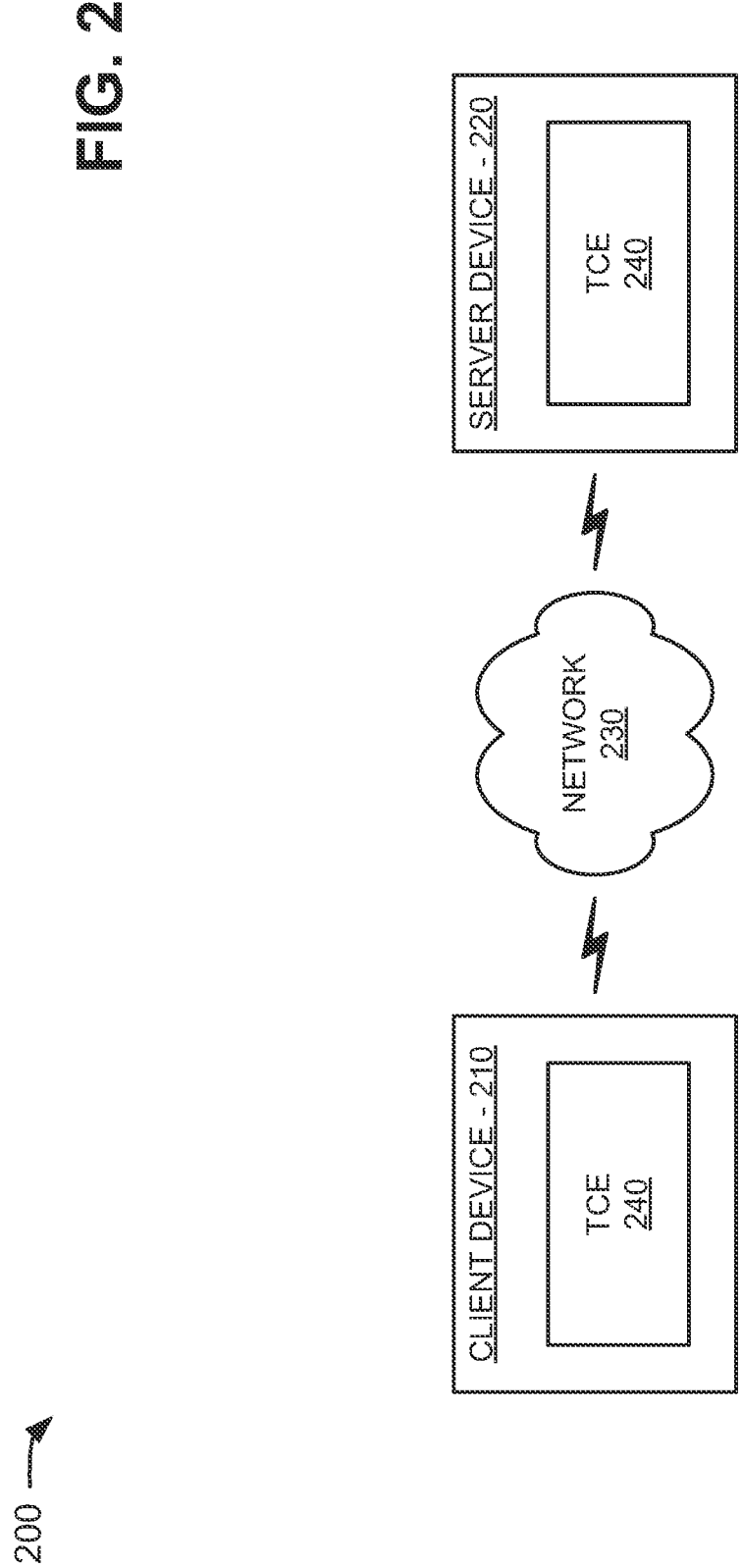
FIG. 2 is a diagram of an example environment in which systems and/or methods described herein may be implemented.

FIG. 2 is a diagram of an example environment 200 in which systems and/or methods described herein may be implemented. As illustrated, environment 200 may include a client device 210 interconnected with a server device 220 via a network 230. Components of environment 200 may interconnect via wired and/or wireless connections. A single client device 210, server device 220, and network 230 have been illustrated in FIG. 2 for simplicity. In practice, environment 200 may include more client devices 210, server devices 220, and/or networks 230. In one example implementation, client device 210 and server device 220 may be provided in a single device or may be provided in separate devices.

Client device 210 may include one or more devices that are capable of communicating with server device 220 via network 230. For example, client device 210 may include a laptop computer, a personal computer, a tablet computer, a desktop computer, a workstation computer, a smart phone, a personal digital assistant (PDA), and/or other computation and communication devices.

Server device 220 may include one or more server devices, or other types of computation and communication devices, that gather, process, and/or provide information in a manner described herein. Server device 220 may include a device that is capable of communicating with client device 210 (e.g., via network 230). In one example, server device 220 may include one or more laptop computers, personal computers, workstation computers, servers, central processing units (CPUs), graphical processing units (GPUs), application-specific integrated circuits (ASICs), field-programmable gate arrays (FPGAs), etc. and/or software (e.g., a simulator) executing on the aforementioned devices. In one example, server device 220 may include TCE 240 and may perform some or all of the functionality described herein for client device 210. Alternatively, server device 220 may be omitted and client device 210 may perform all of the functionality described herein for client device 210.

Network 230 may include a network, such as a local area network (LAN), a wide area network (WAN), a metropolitan area network (MAN), a telephone network, such as the Public Switched Telephone Network (PSTN), an intranet, the Internet, or a combination of networks.

TCE 240 may be provided within a computer-readable medium of client device 210. Alternatively, or additionally, TCE 240 may be provided in another device (e.g., server device 220) that is accessible by client device 210. TCE 240 may include hardware or a combination of hardware and software that provides a computing environment that allows users to perform tasks related to disciplines, such as, but not limited to, mathematics, science, engineering, medicine, business, etc., more efficiently than if the tasks were performed in another type of computing environment, such as an environment that required the user to develop code in a conventional programming language, such as C++, C, Fortran, Pascal, etc. In one implementation, TCE 240 may include a dynamically-typed programming language (e.g., the M language, a MATLAB® language, a MATLAB-compatible language, a MATLAB-like language, etc.) that can be used to express problems and/or solutions in mathematical notations.

For example, TCE 240 may use an array as a basic element, where the array may not require dimensioning. These arrays may be used to support array-based programming where an operation may apply to an entire set of values included in the arrays. Array-based programming may allow array-based operations to be treated as high-level programming that may allow, for example, operations to be performed on entire aggregations of data without having to resort to explicit loops of individual non-array operations. In addition, TCE 240 may be adapted to perform matrix and/or vector formulations that can be used for data analysis, data visualization, application development, simulation, modeling, algorithm development, etc. These matrix and/or vector formulations may be used in many areas, such as statistics, image processing, signal processing, control design, life sciences modeling, discrete event analysis and/or design, state based analysis and/or design, etc.

TCE 240 may further provide mathematical functions and/or graphical tools (e.g., for creating plots, surfaces, images, volumetric representations, etc.). In one implementation, TCE 240 may provide these functions and/or tools using toolboxes (e.g., toolboxes for signal processing, image processing, data plotting, parallel processing, etc.). Alternatively, or additionally, TCE 240 may provide these functions as block sets or in another way, such as via a library, etc.

TCE 240 may be implemented as a text-based environment (e.g., MATLAB software; Octave; Python; Comsol Script; MATRIXx from National Instruments; Mathematica from Wolfram Research, Inc.; Mathcad from Mathsoft Engineering & Education Inc.; Maple from Maplesoft; Extend from Imagine That Inc.; Scilab from The French Institution for Research in Computer Science and Control (INRIA); Virtuoso from Cadence; Modelica or Dymola from Dynasim; etc.); a graphically-based environment (e.g., Simulink® software, Stateflow® software, SimEvents® software, Simscape™ software, etc., by The MathWorks, Inc.; VisSim by Visual Solutions; LabView® by National Instruments; Dymola by Dynasim; SoftWIRE by Measurement Computing; WiT by DALSA Coreco; VEE Pro or SystemVue by Agilent; Vision Program Manager from PPT Vision; Khoros from Khoral Research; Gedae by Gedae, Inc.; Scicos from (INRIA); Virtuoso from Cadence; Rational Rose from IBM; Rhopsody or Tau from Telelogic; Ptolemy from the University of California at Berkeley; aspects of a Unified Modeling Language (UML) or SysML environment; etc.); or another type of environment, such as a hybrid environment that includes one or more of the above-referenced text-based environments and one or more of the above-referenced graphically-based environments.

TCE 240 may include a programming language (e.g., the MATLAB language) that may be used to express problems and/or solutions in mathematical notations. The programming language may be dynamically typed and/or array-based. In a dynamically typed array-based computing language, data may be contained in arrays and data types of the data may be determined (e.g., assigned) at program execution time.

For example, suppose a program, written in a dynamically typed array-based computing language, includes the following statements:

A='hello'
A=int32([1, 2])
A=[1.1, 2.2, 3.3].

Now suppose the program is executed, for example, in a TCE, such as TCE 240. During execution or run-time, when the statement "A='hello'" is executed the data type of variable "A" may be a string data type. Later when the statement "A=int32([1, 2])" is executed the data type of variable "A" may be a 1-by-2 array containing elements whose data type are 32 bit integers. Later, when the statement "A=[1.1, 2.2, 3.3]" is executed, since the language is dynamically typed, the data type of variable "A" may be changed from the above 1-by-2 array to a 1-by-3 array containing elements whose data types are floating point. As can be seen by this example, data in a program written in a dynamically typed array-based computing language may be contained in an array. Moreover, the data type of the data may be determined during execution of the program. Thus, in a dynamically type array-based computing language, data may be represented by arrays and data types of data may be determined at run-time.

TCE 240 may provide mathematical routines and a high-level programming language suitable for non-professional programmers and may provide graphical tools that may be used for creating plots, surfaces, images, volumetric representations, or other representations. TCE 240 may provide these routines and/or tools using toolboxes (e.g., toolboxes for signal processing, image processing, data plotting, parallel processing, etc.). TCE 240 may also provide these routines in other ways, such as, for example, via a library, local or remote database (e.g., a database operating in a computing cloud), remote procedure calls (RPCs), and/or an application programming interface (API). TCE 240 may be configured to improve runtime performance when performing computing operations. For example, TCE 240 may include a just-in-time (JIT) compiler.

Although FIG. 2 shows example components of environment 200, in other implementations, environment 200 may include fewer components, different components, differently arranged components, and/or additional components than those depicted in FIG. 2. Alternatively, or additionally, one or more components of environment 200 may perform one or more other tasks described as being performed by one or more other components of environment 200.

Example Device Architecture

Figure 3:
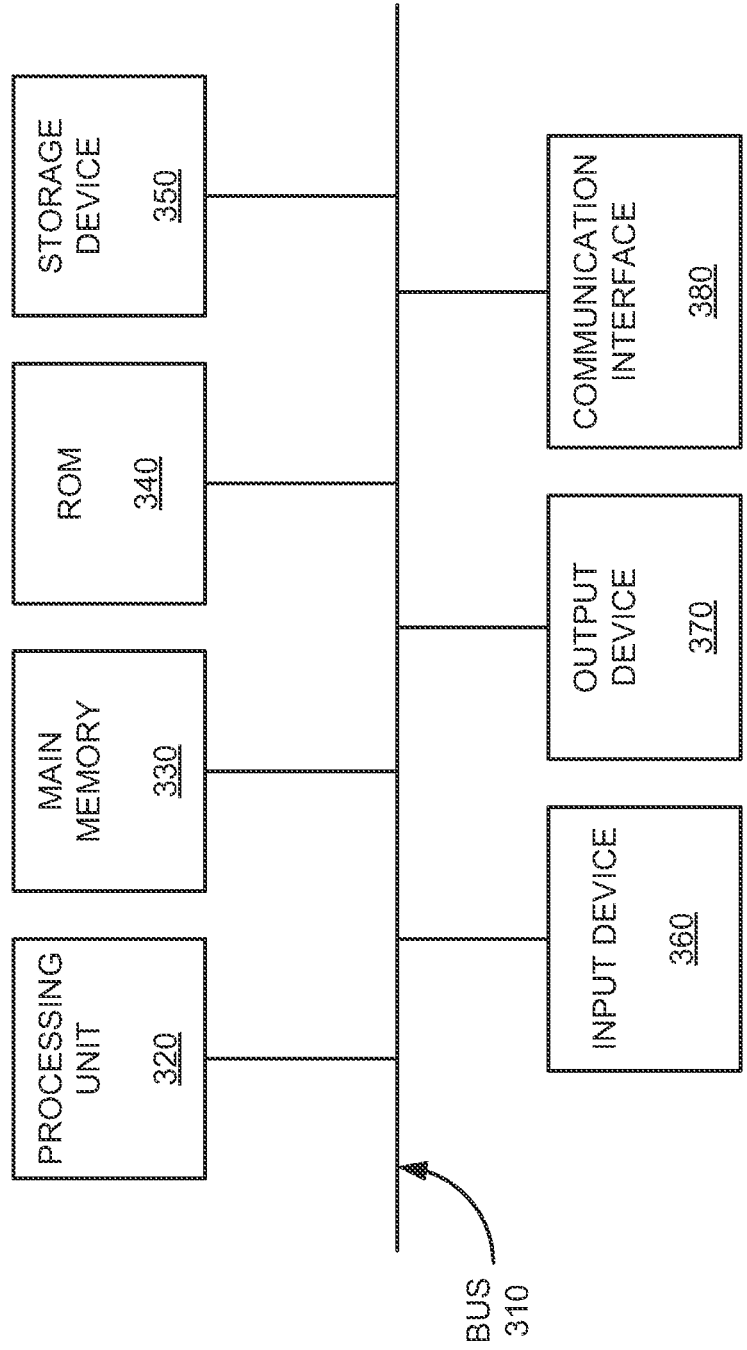
FIG. 3 is a diagram of example components of one or more of the devices of the environment depicted in FIG. 2.

FIG. 3 is an example diagram of a device 300 that may correspond to one or more of the devices of environment 200. As illustrated, device 300 may include a bus 310, a processing unit 320, a main memory 330, a read-only memory (ROM) 340, a storage device 350, an input device 360, an output device 370, and/or a communication interface 380. Bus 310 may include a path that permits communication among the components of device 300.

Processing unit 320 may include one or more processors, microprocessors, or other types of processing units that may interpret and execute instructions. Main memory 330 may include one or more random access memories (RAMs) or other types of dynamic storage devices that may store information and/or instructions for execution by processing unit 320. ROM 340 may include one or more ROM devices or other types of static storage devices that may store static information and/or instructions for use by processing unit 320. Storage device 350 may include a magnetic and/or optical recording medium and its corresponding drive.

Input device 360 may include a mechanism that permits a user to input information to device 300, such as a keyboard, a camera, an accelerometer, a gyroscope, a mouse, a pen, a microphone, voice recognition and/or biometric mechanisms, a remote control, a touch screen, a neural interface, etc. Output device 370 may include a mechanism that outputs information to the user, including a display, a printer, a speaker, etc. Communication interface 380 may include any transceiver-like mechanism that enables device 300 to communicate with other devices, networks, and/or systems. For example, communication interface 380 may include mechanisms for communicating with another device or system via a network.

As described herein, device 300 may perform certain operations in response to processing unit 320 executing software instructions contained in a computer-readable medium, such as main memory 330. A computer-readable medium may be defined as a non-transitory memory device. A memory device may include space within a single physical memory device or spread across multiple physical memory devices. The software instructions may be read into main memory 330 from another computer-readable medium, such as storage device 350, or from another device via communication interface 380. The software instructions contained in main memory 330 may cause processing unit 320 to perform processes described herein. Alternatively, hardwired circuitry may be used in place of or in combination with software instructions to implement processes described herein. Thus, implementations described herein are not limited to any specific combination of hardware circuitry and software.

Although FIG. 3 shows example components of device 300, in other implementations, device 300 may include fewer components, different components, differently arranged components, and/or additional components than depicted in FIG. 3. Alternatively, or additionally, one or more components of device 300 may perform one or more other tasks described as being performed by one or more other components of device 300.

Example Technical Computing Environment

Figure 4:
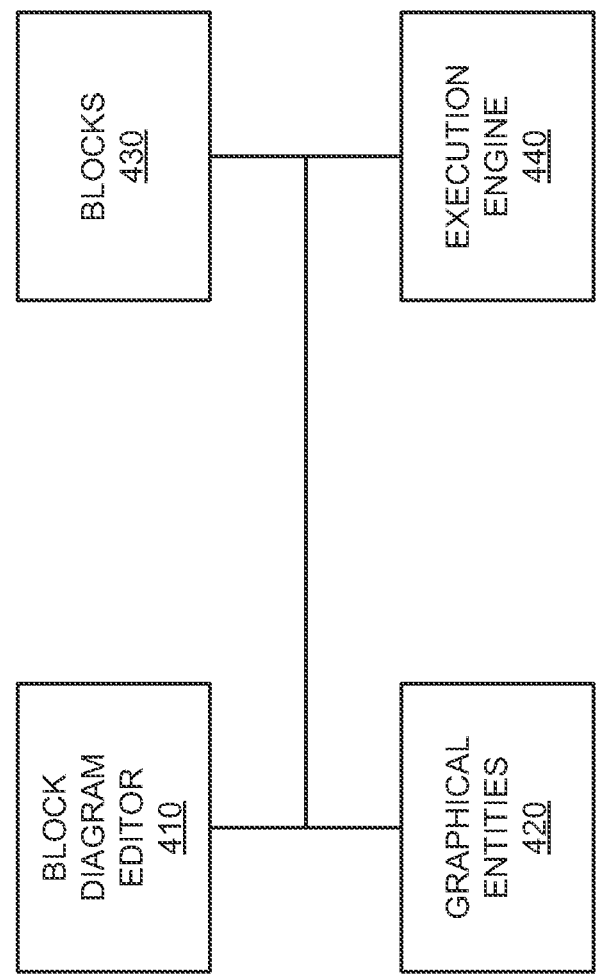
FIG. 4 is a diagram of example functional components of a technical computing environment (TCE) that may be used by one or more of the devices of the environment depicted in FIG. 2.

FIG. 4 is a diagram of example functional components of TCE 240. In one implementation, the functions described in connection with FIG. 4 may be performed by one or more components of device 300 (FIG. 3) and/or by one or more devices 300. As shown in FIG. 4, TCE 240 may include a block diagram editor 410, graphical entities 420, blocks 430, and/or an execution engine 440.

Block diagram editor 410 may include hardware or a combination of hardware and software that may be used to graphically specify models of dynamic systems. In one implementation, block diagram editor 410 may permit a user to perform actions, such as construct, edit, display, annotate, save, and/or print a graphical model (e.g., a block diagram that visually and/or pictorially represents a dynamic system). In another implementation, block diagram editor 410 may permit a user to create and/or store data relating to graphical entities 420.

A textual interface may be provided to permit interaction with block diagram editor 410. A user may write scripts that perform automatic editing operations on a model using the textual interface. For example, the textual interface may provide a set of windows that may act as a canvas for the model, and may permit user interaction with the model. A model may include one or more windows depending on whether the model is partitioned into multiple hierarchical levels.

Graphical entities 420 may include hardware or a combination of hardware and software that may provide entities (e.g., signal lines, buses, etc.) that represent how data may be communicated between functional and/or non-functional units and blocks 430 of a model. Blocks 430 may include fundamental mathematical elements of a block diagram model.

Execution engine 440 may include hardware or a combination of hardware and software that may process a graphical model to produce simulation results, may convert the graphical model into executable code, and/or may perform other analyses and/or related tasks. In one implementation, for a block diagram graphical model, execution engine 440 may translate the block diagram into executable entities (e.g., units of execution) following the layout of the block diagram. The executable entities may be compiled and/or executed on a device (e.g., client device 210) to implement the functionality specified by the model.

Graphical models may include entities with relationships between the entities, and the relationships and/or the entities may have attributes associated with them. The entities my include model elements such as blocks 430 and ports. The relationships may include model elements such as lines (e.g., connector lines) and references. The attributes may include model elements such as value information and meta information for the model element associated with the attributes. Graphical models may be associated with configuration information. The configuration information may include information for the graphical model such as model execution information (e.g., numerical integration schemes, fundamental execution period, etc.), model diagnostic information (e.g., whether an algebraic loop should be considered an error or result in a warning), model optimization information (e.g., whether model elements should share memory during execution), model processing information (e.g., whether common functionality should be shared in code that is generated for a model), etc.

Additionally, or alternatively, a graphical model may have executable semantics and/or may be executable. An executable graphical model may be a time based block diagram. A time based block diagram may consist, for example, of blocks (e.g., blocks 430) connected by lines (e.g., connector lines). The blocks may consist of elemental dynamic systems such as a differential equation system (e.g., to specify continuous-time behavior), a difference equation system (e.g., to specify discrete-time behavior), an algebraic equation system (e.g., to specify constraints), a state transition system (e.g., to specify finite state machine behavior), an event based system (e.g., to specify discrete event behavior), etc. The lines may represent signals (e.g., to specify input/output relations between blocks or to specify execution dependencies between blocks), variables (e.g., to specify information shared between blocks), physical connections (e.g., to specify electrical wires, pipes with volume flow, rigid mechanical connections, etc.), etc. The attributes may consist of meta information such as sample times, dimensions, complexity (whether there is an imaginary component to a value), data type, etc. associated with the model elements.

In a time based block diagram, ports may be associated with blocks (e.g., blocks 430). A relationship between two ports may be created by connecting a line (e.g., a connector line) between the two ports. Lines may also, or alternatively, be connected to other lines, for example by creating branch points. For instance, three or more ports can be connected by connecting a line to each of the ports, and by connecting each of the lines to a common branch point for all of the lines. A common branch point for the lines that represent physical connections may be a dynamic system (e.g., by summing all variables of a certain type to 0 or by equating all variables of a certain type). A port may be an input port, an output port, an enable port, a trigger port, a function-call port, a publish port, a subscribe port, an exception port, an error port, a physics port, an entity flow port, a data flow port, a control flow port, etc.

Relationships between blocks (e.g., blocks 430) may be causal and/or non-causal. For example, a model may include a block that represents a continuous-time integration block that may be causally related to a data logging block by using a line (e.g., a connector line) to connect an output port of the continuous-time integration block to an input port of the data logging block. Further, during execution of the model, the value stored by the continuous-time integrator may change as the current time of the execution progresses. The value of the state of the continuous-time integrator may be available on the output port and the connection with the input port of the data logging block may make this value available to the data logging block.

A sample time may be associated with the elements of a graphical model. For example, a graphical model may include a block (e.g., block 430) with a continuous sample time such as a continuous-time integration block that may integrate an input value as time of execution progresses. This integration may be specified by a differential equation. During execution, the continuous-time behavior may be approximated by a numerical integration scheme that is part of a numerical solver. The numerical solver may take discrete steps to advance the execution time, and these discrete steps may be constant during an execution (e.g., fixed step integration) or may be variable during an execution (e.g., variable-step integration).

Alternatively, or additionally, a graphical model may include a block (e.g., block 430) with a discrete sample time such as a unit delay block that may output values of a corresponding input after a specific delay. This delay may be a time interval and this interval may determine a sample time of the block. During execution, the unit delay block may be evaluated each time the execution time has reached a point in time where an output of the unit delay block may change. These points in time may be statically determined based on a scheduling analysis of the graphical model before starting execution.

Alternatively, or additionally, a graphical model may include a block (e.g., block 430) with an asynchronous sample time, such as a function-call generator block that may schedule a connected block to be evaluated at a non-periodic time. During execution, a function-call generator block may evaluate an input and when the input attains a specific value when the execution time has reached a point in time, the function-call generator block may schedule a connected block to be evaluated at this point in time and before advancing execution time.

Further, the values of attributes of a graphical model may be inferred from other elements of the graphical model or attributes of the graphical model. For example, the graphical model may include a block (e.g., block 430), such as a unit delay block, that may have an attribute that specifies a sample time of the block. When a graphical model has an execution attribute that specifies a fundamental execution period, the sample time of the unit delay block may be inferred from this fundamental execution period.

As another example, the graphical model may include two unit delay blocks (e.g., blocks 430) where the output of the first of the two unit delay blocks is connected to the input of the second of the two unit delay block. The sample time of the first unit delay block may be inferred from the sample time of the second unit delay block. This inference may be performed by propagation of model element attributes such that after evaluating the sample time attribute of the second unit delay block, a graph search proceeds by evaluating the sample time attribute of the first unit delay block since it is directly connected to the second unit delay block.

The values of attributes of a graphical model may be set to characteristics settings, such as one or more inherited settings, one or more default settings, etc. For example, the data type of a variable that is associated with a block (e.g., block 430) may be set to a default such as a double. Because of the default setting, an alternate data type (e.g., a single, an integer, a fixed point, etc.) may be inferred based on attributes of elements that the graphical model comprises (e.g., the data type of a variable associated with a connected block) and/or attributes of the graphical model. As another example, the sample time of a block may be set to be inherited. In case of an inherited sample time, a specific sample time may be inferred based on attributes of elements that the graphical model comprises and/or attributes of the graphical model (e.g., a fundamental execution period).

Although FIG. 4 shows example functional components of TCE 240, in other implementations, TCE 240 may include fewer functional components, different functional components, differently arranged functional components, and/or additional functional components than depicted in FIG. 4. Alternatively, or additionally, one or more functional components of TCE 240 may perform one or more other tasks described as being performed by one or more other functional components of TCE 240.

Example Technical Computing Environment Operations

Figure 5:
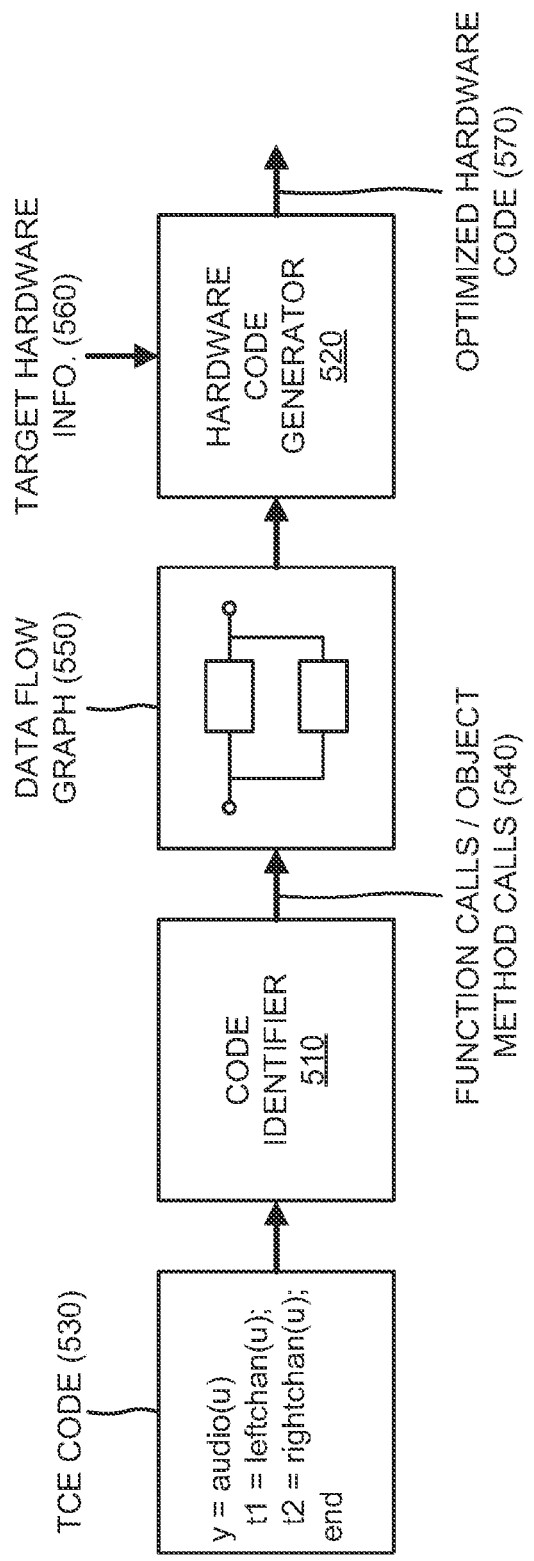
FIG. 5 is a diagram of example operations capable of being performed by the TCE.

FIG. 5 is a diagram of example operations 500 capable of being performed by TCE 240 (FIGS. 2-4). TCE 240 may include the features described above in connection with, for example, one or more of FIGS. 1-4. As illustrated in FIG. 5, TCE 240 may include a code identifier component 510 and a hardware code generator component 520. The functions described in connection with code identifier component 510 and hardware code generator component 520 may be performed by one or more components of device 300 (FIG. 3) and/or by one or more devices 300.

Code identifier component 510 may receive code 530 generated by TCE 240. TCE code 530 may include text-based code that may require further processing to execute, binary code that may be executed, text files that may be executed in conjunction with other executables, etc. In one example, TCE code 530 may include the following syntax:

```
y = audio-equalizer (u);
    t1 = leftchannel-processing(u);
    t2 = rightchannel-processing(u);
    if (t1 > t2)
        y = t1;
    else
        y = t2;
    end
end.
```

Code identifier component 510 may identify one or more function calls and/or object method calls in TCE code 530, as indicated by reference number 540. In the example TCE code 530, code identifier component 510 may identify t1=leftchannel-processing(u) and t2=rightchannel-processing(u) as function calls in TCE code 530. In one example, code identifier component 510 may use data types, sizes, complexity, etc. information associated with TCE code 530 to infer or identify a hierarchy of function calls/object method calls 540 in TCE code 530. Code identifier component 510 may identify function calls/object method calls 540 in TCE code 530 when TCE code 530 is being compiled or before or after TCE code 530 is compiled.

Code identifier component 510 may create a control flow graph, for TCE code 530, based on the identified function calls and/or object method calls 540. The control flow graph may preserve the hierarchy of the identified function calls and/or object method calls 540. The control flow graph may not change function call hierarchy in TCE code 530, but may contain functions of TCE code 530 and/or calls to those functions. Nodes of a data structure of the control flow graph may be traversed to identify function and/or method calls. Code identifier component 510 may take TCE code 530 and create a control flow graph intermediate representation. Code identifier component 510 may process the control flow graph in multiple analysis, translation, and/or optimization stages (e.g., for efficiency and scalability) to create an internal representation suitable for detecting function calls and/or system object method calls in TCE code 530. In one example, code identifier component 510 may identify system object method calls and/or function calls in procedural and untimed TCE code 530.

Code identifier component 510 may convert the identified system object method calls and/or function calls into a data flow, and may extract parallelism from the data flow. For example, code identifier component 510 may convert procedural languages (e.g., Fortran, C, MATLAB, etc.), in the control flow graph, into data driven execution (e.g., Simulink) in a data flow graph 550. Alternatively, or additionally, code identifier component 510 may convert sequential machines (e.g., assembly or C language on processors), in the control flow graph, into parallel machines (e.g., HDL on hardware, C on GPUs, Simulink, etc.) in data flow graph 550.

Such operations may transform the control flow graph into data flow graph 550. Data flow graph 550 may include nodes and/or signals provided between the nodes. The nodes may include representations of function calls/object method calls 540 that are to be executed by one or more hardware devices (e.g., a CPU, a GPU, one or more cores of a CPU or GPU, etc.) of an architecture model. The signals may include representations of connections (e.g., communication interfaces and/or channels) provided between function calls/object method calls 540. Edges of data flow graph 550 may have timing inferred automatically. The transformation to data flow graph 550 may ensure that latency changes are introduced without affecting any numerical differences in TCE code 530. Code identifier component 510 may infer timing by analysis of the control flow graph and by converting the control flow graph to data flow graph 550 in the presence of function calls and/or system object calls.

In one example, a function (e.g., biquad filter) may be called a number (e.g., numSections) of times in the following TCE code 530:

```
function y = mlhdlc_iir_filter(x, sos, g)
% Declare persistent variables and initialize
numSections = numel(sos)/6;
persistent z
if isempty(z)
    z = zeros(numSections, 2);
end
y = x;
for i=coder.unroll(1:numSections)
    curSOS = sos((i-1)*6+1:i*6);
    [y z(i,:)] = biquad_filter(y, curSOS(1:3), curSOS(4: 6), z(i, :));
end
y = y * g;
end
function [y, z] = biquad_filter (x, b, a, z)
% a(1) is assumed to be 1
% Direct-form II implementation
tmp = x - z(1) *a(2) - z(2) *a(3);
y = z(2) * b(3) + z(1) * b(2) + tmp * b(1);
z(2) = z(1);
z(1) = tmp;
end.
```

Code identifier component 510 may recognize the function call and may provide code level folding of the function to fully parallelize execution in hardware. If code identifier component 510 identifies a function call while traversing the control flow graph, code identifier component 510 may utilize content of the function to create a reusable (e.g., a partition) component and a fully independent stand alone parallel node in data flow graph 550. If code identifier component 510 identifies another function call, code identifier component 510 may determine whether the other function call is the same as the previously identified function call. If the other function call is the same as the previously identified function call, code identifier component 510 may link the other function call to the same reusable component. If the other function call is not the same as the previously identified function call, code identifier component 510 may create a new reusable component. After identifying all of the function calls, code identifier component 510 may create a fully formed data flow graph 550 when function calls and/or system object method calls become nodes of data flow graph 550.

Function call hierarchy of TCE code 530 may be independent of data typing. The control flow graph may be created with data types inferred from TCE code 530. The data types may not affect function call hierarchy in the control flow graph. Depending on the kinds of data types used in calling functions, the control flow graph may have multiple function call statements with different kinds of inputs. Code identifier component 510 may transform the multiple function call statements into data flow graph 550, as described above.

As further shown in FIG. 5, code identifier component 510 may provide data flow graph 550 to hardware code generator component 520. Hardware code generator component 520 may receive data flow graph 550, and may receive target hardware information 560 (e.g., from a user of TCE 240). Target hardware information 560 may include information associated with a hardware device(s) (e.g., of the architecture model) upon which TCE code 530 is to be executed. Hardware code generator component 520 may generate optimized hardware code 570 based on data flow graph 550 and target hardware information 560. In one implementation, hardware code 570 may be optimized by enabling function calls/object method calls 540 to be executed in parallel and/or to share the hardware device(s) during execution. Optimized hardware code 570 may be executed by the hardware device(s) associated with target hardware information 560.

In one example, hardware code generator component 520 may determine that TCE code 530 includes function calls/object method calls 540 that may be executed in parallel. Hardware code generator component 520 may configure hardware code 570 to execute such function calls/object method calls 540 in parallel, which may conserve execution time of hardware code 570. Alternatively, or additionally, hardware code generator component 520 may determine that the function calls (e.g., t1=leftchannel-processing(u) and t2=rightchannel-processing(u)) in TCE code 530 are identical and require the same hardware devices. Hardware code generator component 520 may configure hardware code 570 to utilize the same hardware device (e.g., rather than two separate hardware devices) for the function calls, which may conserve hardware resources.

Alternatively, or additionally, hardware code generator component 520 may output (e.g., provide for display) and/or store hardware code 570. Hardware code generator component 520 may provide, in a graphical view, traceability between TCE 240 and the identified function calls/object method calls 540, in addition to the generated hardware code 570.

Although FIG. 5 shows example operations capable of being performed by TCE 240, in other implementations, TCE 240 may perform fewer operations, different operations, and/or additional operations than depicted in FIG. 5. Alternatively, or additionally, one or more components of FIG. 5 may perform one or more other tasks described as being performed by one or more other components of FIG. 5.

Figure 6:
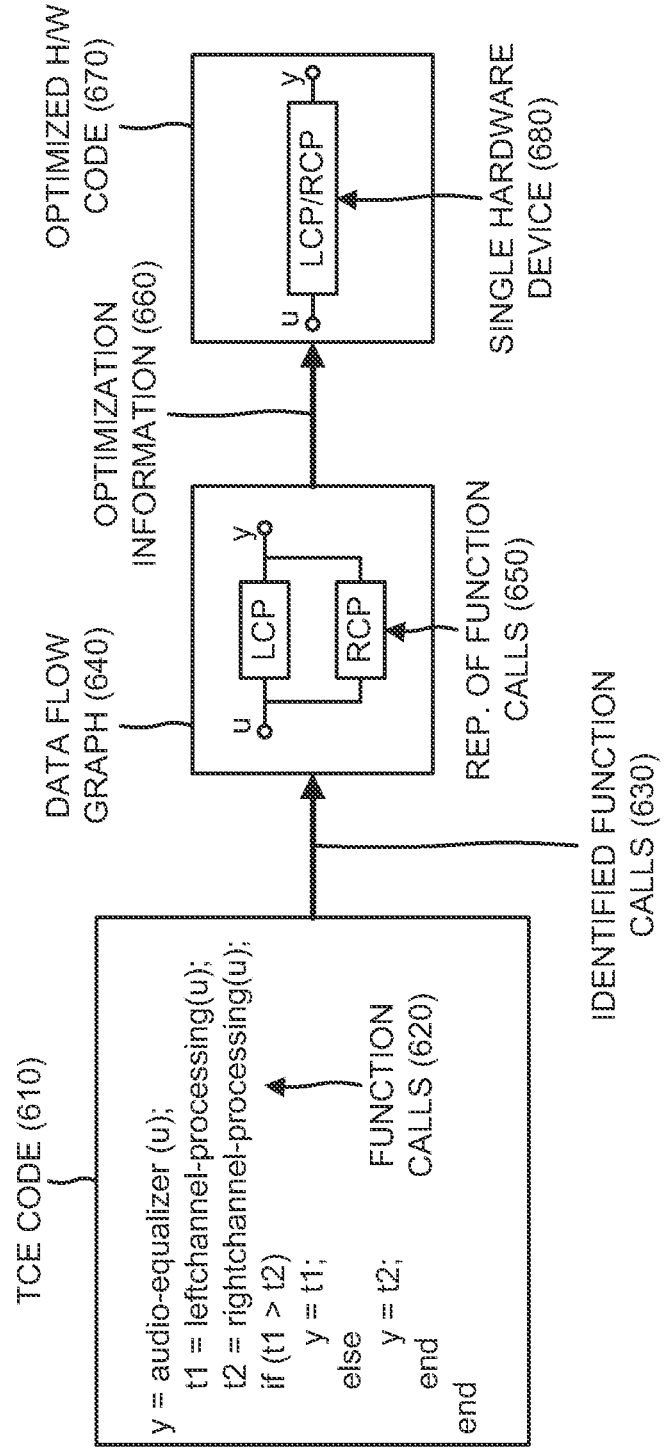
FIG. 6 is a diagram of example function call operations capable of being performed by the TCE.

FIG. 6 is a diagram of example function call operations 600 capable of being performed by TCE 240. TCE 240 may include the features described above in connection with, for example, one or more of FIGS. 1-5. As illustrated in FIG. 6, TCE 240 (e.g., code identifier component 510, not shown) may receive code 610 generated by TCE 240. In one example, TCE code 610 may include the following syntax:

```
y = audio-equalizer (u);
    t1 = leftchannel-processing(u);
    t2 = rightchannel-processing(u);
    if (t1 > t2)
        y = t1 ;
    else
        y = t2;
    end
end.
```

TCE 240 (e.g., code identifier component 510) may identify one or more function calls 620 in TCE code 610. In the example TCE code 610, TCE 240 (e.g., code identifier component 510) may identify t1=leftchannel-processing(u) and t2=rightchannel-processing(u) as function calls 620. In one implementation, TCE 240 may use data types, sizes, complexity, etc. information associated with TCE code 610 to infer or identify a hierarchy of function calls 620 in TCE code 610. TCE 240 may utilize the identified function calls 620, as indicated by reference number 630, to create a data flow graph 640.

Data flow graph 640 may include nodes and/or signals provided between the nodes. The nodes may include representations 650 of function calls 620 that are to be executed by one or more hardware devices (e.g., a CPU, a GPU, one or more cores of a CPU or GPU, etc.) of an architecture model. In one example, data flow graph 640 may include a first representation 650 (e.g., a node labeled "LCP") for a first function call 620 (e.g., t1=leftchannel-processing(u)), and a second representation 650 (e.g., a node labeled "RCP") for a second function call 620 (e.g., t2=rightchannel-processing (u)). The signals may include representations of connections (e.g., communication interfaces and/or channels) provided between function calls 620.

TCE 240 (e.g., hardware code generator component 520, not shown) may determine optimization information 660 for data flow graph 640. Optimization information 660 may include target hardware information 560 (FIG. 5), information identifying that hardware code, generated from data flow graph 640, may be optimized by enabling function calls 620 to be executed in parallel and/or to share the hardware devices during execution, etc. TCE 240 (e.g., hardware code generator component 520) may generate optimized hardware code 670 based on data flow graph 640 and/or optimization information 660.

In one example, TCE 240 (e.g., hardware code generator component 520) may determine that function calls 620 (e.g., t1=leftchannel-processing(u) and t2=rightchannel-processing(u)) are identical and require the same hardware devices. TCE 240 (e.g., hardware code generator component 520) may configure hardware code 670 to utilize a single hardware device 680 (e.g., rather than two separate hardware devices) for function calls 620. As shown in FIG. 6, the two representations 650 (e.g., the LCP node and the RCP node) for function calls 620 may be merged into a single representation (e.g., a node labeled "LCP/RCP") that may be executed on single hardware device 680.

Although FIG. 6 shows example function call operations capable of being performed by TCE 240, in other implementations, TCE 240 may perform fewer operations, different operations, and/or additional operations than depicted in FIG. 6. Alternatively, or additionally, one or more components of FIG. 6 may perform one or more other tasks described as being performed by one or more other components of FIG. 6.

Figure 7:
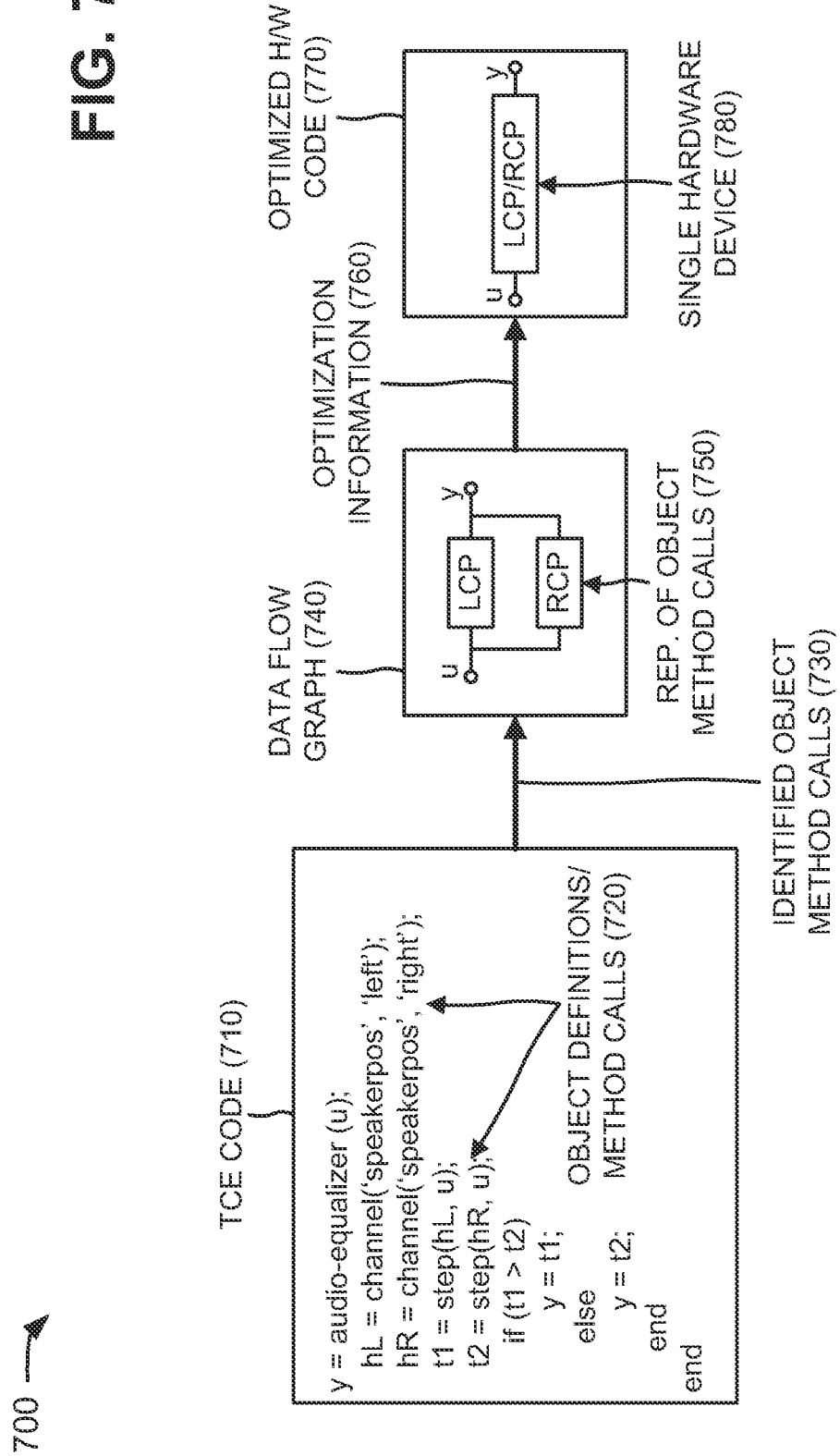
FIG. 7 is a diagram of example object method call operations capable of being performed by the TCE.

FIG. 7 is a diagram of example object method call operations 700 capable of being performed by TCE 240. TCE 240 may include the features described above in connection with, for example, one or more of FIGS. 1-6. As illustrated in FIG. 7, TCE 240 (e.g., code identifier component 510, not shown) may receive code 710 generated by TCE 240. In one example, TCE code 710 may include the following syntax:

```
y = audio-equalizer (u);
    hL = channel('speakerpos', 'left');
    hR = channel('speakerpos', 'right');
    t1 = step(hL, u);
    t2 = step(hR, u);
    if (t1 > t2)
        y = t1;
    else
        y = t2;
    end
end.
```

TCE 240 (e.g., code identifier component 510) may identify one or more object definitions and/or one or more object definitions/method calls 720 in TCE code 710. In the example TCE code 710, TCE 240 (e.g., code identifier component 510) may identify hL=channel('speakerpos', 'left') and hR=channel('speakerpos', 'right') as object definitions, and may identify as t1=step(hL, u) and t2=step(hR, u) as object method calls. In one implementation, TCE 240 may use data types, sizes, complexity, etc. information associated with TCE code 710 to infer or identify a hierarchy of object definitions/method calls 720 in TCE code 710. TCE 240 may utilize the identified object definitions/method calls 720, as indicated by reference number 730, to create a data flow graph 740.

Data flow graph 740 may include nodes and/or signals provided between the nodes. The nodes may include representations 750 of object definitions/method calls 720 that are to be executed by one or more hardware devices (e.g., a CPU, a GPU, one or more cores of a CPU or GPU, etc.) of an architecture model. In one example, data flow graph 740 may include a first representation 750 (e.g., a node labeled "LCP") for a first object method call 720 (e.g., t1=step(hL, u)), and a second representation 750 (e.g., a node labeled "RCP") for a second object method call 720 (e.g., t2=step(hR, u)). The signals may include representations of connections (e.g., communication interfaces and/or channels) provided between object definitions/method calls 720.

TCE 240 (e.g., hardware code generator component 520, not shown) may determine optimization information 760 for data flow graph 740. Optimization information 760 may include target hardware information 560 (FIG. 5), information identifying that hardware code, generated from data flow graph 740, may be optimized by enabling object definitions/method calls 720 to be executed in parallel and/or to share the hardware devices during execution, etc. TCE 240 (e.g., hardware code generator component 520) may generate optimized hardware code 770 based on data flow graph 740 and/or optimization information 760.

In one example, TCE 240 (e.g., hardware code generator component 520) may determine that object definitions/method calls 720 (e.g., hL=channel('speakerpos', 'left') and hR=channel('speakerpos', 'right')) are identical and require the same hardware devices. TCE 240 (e.g., hardware code generator component 520) may configure hardware code 770 to utilize a single hardware device 780 (e.g., rather than two separate hardware devices) for object definitions/method calls 720. As shown in FIG. 7, the two representations 750 (e.g., the LCP node and the RCP node) for object definitions/method calls 720 may be merged into a single representation (e.g., a node labeled "LCP/RCP") that may be executed on single hardware device 780.

Although FIG. 7 shows example object method call operations capable of being performed by TCE 240, in other implementations, TCE 240 may perform fewer operations, different operations, and/or additional operations than depicted in FIG. 7. Alternatively, or additionally, one or more components of FIG. 7 may perform one or more other tasks described as being performed by one or more other components of FIG. 7.

Figure 8:
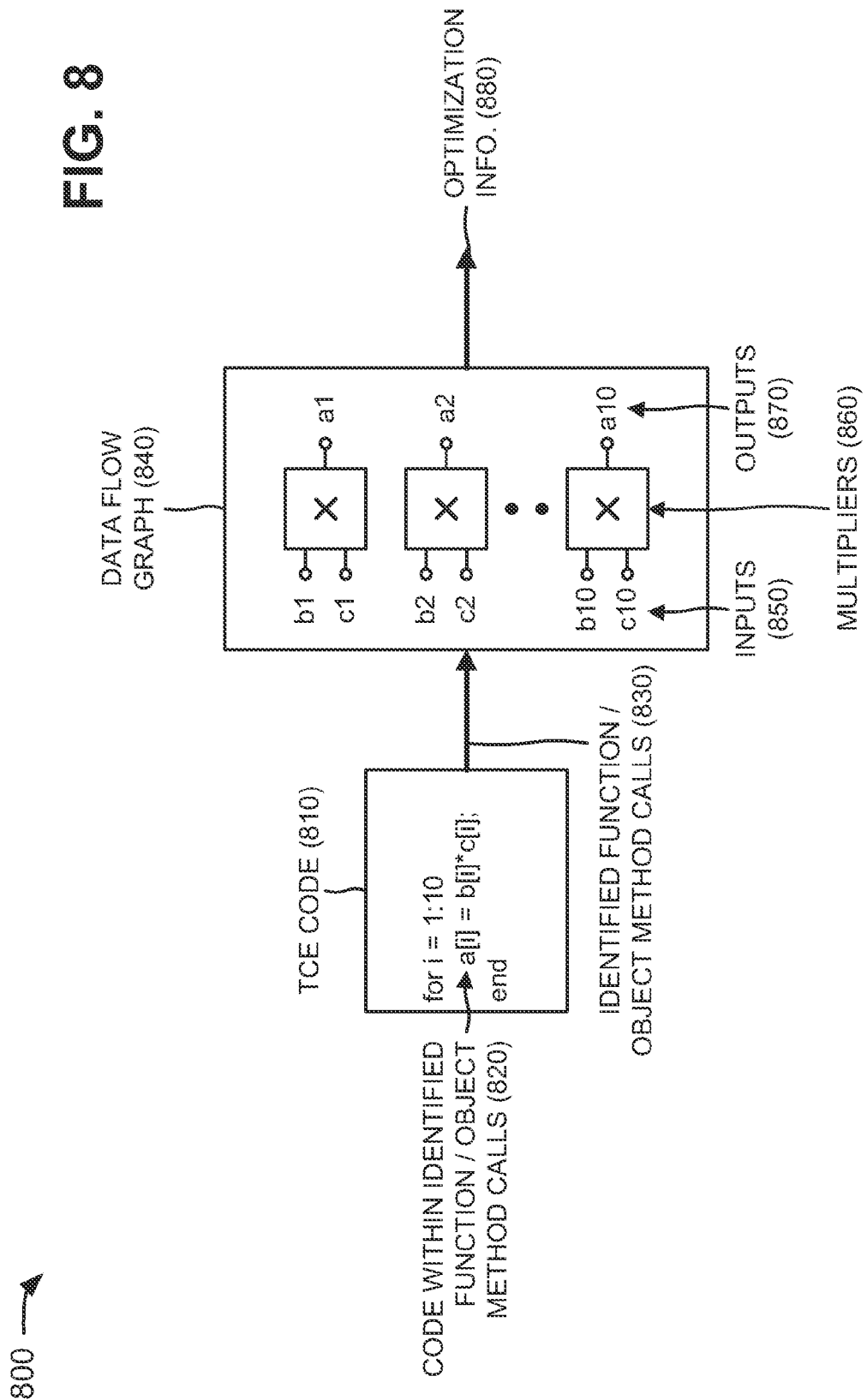
FIG. 8 is a diagram of example operations capable of being performed by a code identifier component of the TCE.

FIG. 8 is a diagram of example operations 800 capable of being performed by code identifier component 510 of TCE 240. TCE 240 and code identifier component 510 may include the features described above in connection with, for example, one or more of FIGS. 1-7. As illustrated in FIG. 8, code identifier component 510 may receive code 810 generated by TCE 240. In one example, TCE code 810 may include the following syntax:

```
for i = 1:10
    a[i] = b[i] *c[i];
end.
```

Code identifier component 510 may identify code 820 within identified one or more function/object method calls in TCE code 810. In the example TCE code 810, code identifier component 510 may identify a[i]=b[i]*c[i] as code 820 within an identified function/object method call. In one implementation, code identifier component 510 may use data types, sizes, complexity, etc. information associated with TCE code 810 to infer or identify a hierarchy of code 820 within identified function/object method calls in TCE code 810. Code identifier component 510 may utilize code 820 within identified function/object method calls, as indicated by reference number 830, to create a data flow graph 840.

Data flow graph 840 may include nodes and/or signals provided between the nodes. The nodes may include representations of code 820 within identified function/object method calls that are to be executed by one or more hardware devices of an architecture model. The signals may include representations of connections provided between code 820 within identified function/object method calls. In one example, data flow graph 840 may include inputs 850 (e.g., b1 through b10 and c1 through c10), multipliers 860, and outputs 870 (e.g., a1 through a10). Inputs 850 may include input variables to a multiplication function. Multipliers 860 may include representations (e.g., nodes) of a function that multiplies inputs 850. For example, a first multiplier 860 may multiply inputs 850 (e.g., b1 and c1), a second multiplier 860 may multiply inputs 850 (e.g., b2 and c2), etc. Outputs 870 may include output variables of the multiplication function.

Code identifier component 510 may determine optimization information 880 from data flow graph 840. Optimization information 880 may include target hardware information 560 (FIG. 5), information identifying that hardware code, generated from data flow graph 840, may be optimized by enabling code 820 within identified function/object method calls to be executed in parallel. Hardware code generator component 520 (not shown) may generate optimized hardware code based on data flow graph 840 and/or optimization information 880. If optimization information 880 indicates that hardware code cannot be executed in parallel, hardware code generator component 520 (not shown) may generate optimized hardware code that serially executes code 820 within identified function/object method calls.

Although FIG. 8 shows example operations capable of being performed by code identifier component 510, in other implementations, code identifier component 510 may perform fewer operations, different operations, and/or additional operations than depicted in FIG. 8. Alternatively, or additionally, one or more components of FIG. 8 may perform one or more other tasks described as being performed by one or more other components of FIG. 8.

Figure 9:
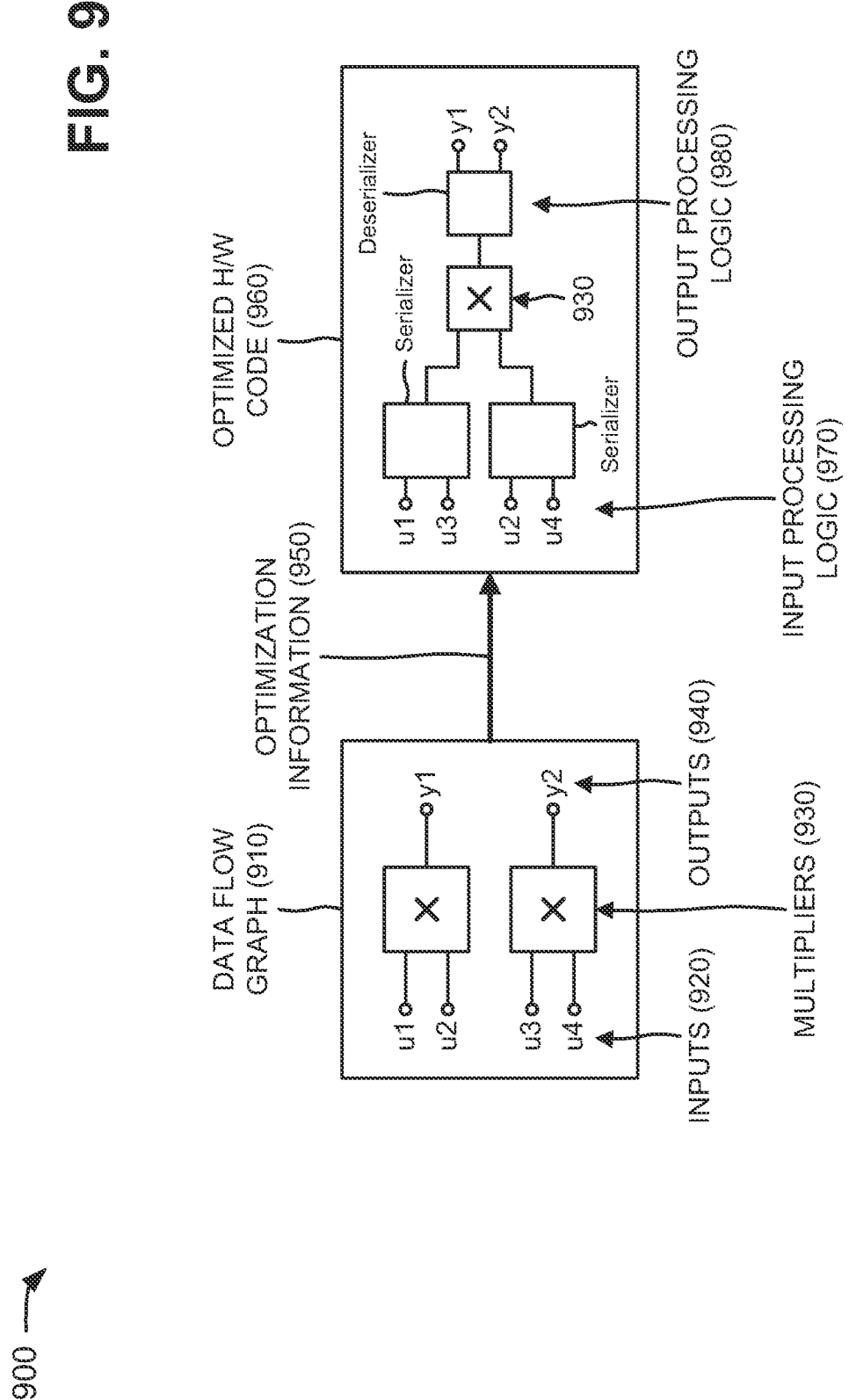
FIG. 9 is a diagram of example operations capable of being performed by a hardware code generator component of the TCE.

FIG. 9 is a diagram of example operations 900 capable of being performed by hardware code generator component 520 of TCE 240. TCE 240 and hardware code generator component 520 may include the features described above in connection with, for example, one or more of FIGS. 1-8. As illustrated in FIG. 9, hardware code generator component 520 may receive a data flow graph 910 that includes inputs 920 (e.g., u1, u2, u3, and u4), two multipliers 930, and outputs 940 (e.g., y1 and y2).

Inputs 920 may include input variables to a multiplication function. Multipliers 930 may include representations (e.g., nodes) of a function that multiplies inputs 920. For example, a first multiplier 930 may multiply inputs 920 (e.g., u1 and u2), and a second multiplier 930 may multiply inputs 920 (e.g., u3 and u4). Outputs 940 may include output variables of the multiplication function.

Hardware code generator component 520 may determine optimization information 950 for data flow graph 910. Optimization information 950 may include target hardware information 560 (FIG. 5), information identifying that hardware code, generated from data flow graph 910, may be optimized by enabling multipliers 930 to share the same hardware device during execution, etc. Hardware code generator component 520 may generate optimized hardware code 960 based on data flow graph 910 and/or optimization information 950.

In one example, hardware code generator component 520 may determine that multipliers 930 are identical (e.g., perform the same function) and require the same hardware devices. Hardware code generator component 520 may configure hardware code 960 to utilize a single hardware device (e.g., rather than two separate hardware devices) for a single multiplier 930. As shown in FIG. 8, the two multipliers 930 may be merged into a single multiplier 930 that may be executed on a single hardware device. Optimized hardware code 960 may include input processing logic 970 that provides the correct inputs 920 to the single multiplier 930. As further shown, optimized hardware code 960 may include output processing logic 980 that provides the correct outputs 940 from the single multiplier 930. In such an arrangement, the single multiplier 930 may provide a faster rate of processing.

Although FIG. 9 shows example operations capable of being performed by hardware code generator component 520, in other implementations, hardware code generator component 520 may perform fewer operations, different operations, and/or additional operations than depicted in FIG. 9. Alternatively, or additionally, one or more components of FIG. 9 may perform one or more other tasks described as being performed by one or more other components of FIG. 9.

Example Process

Figure 10:
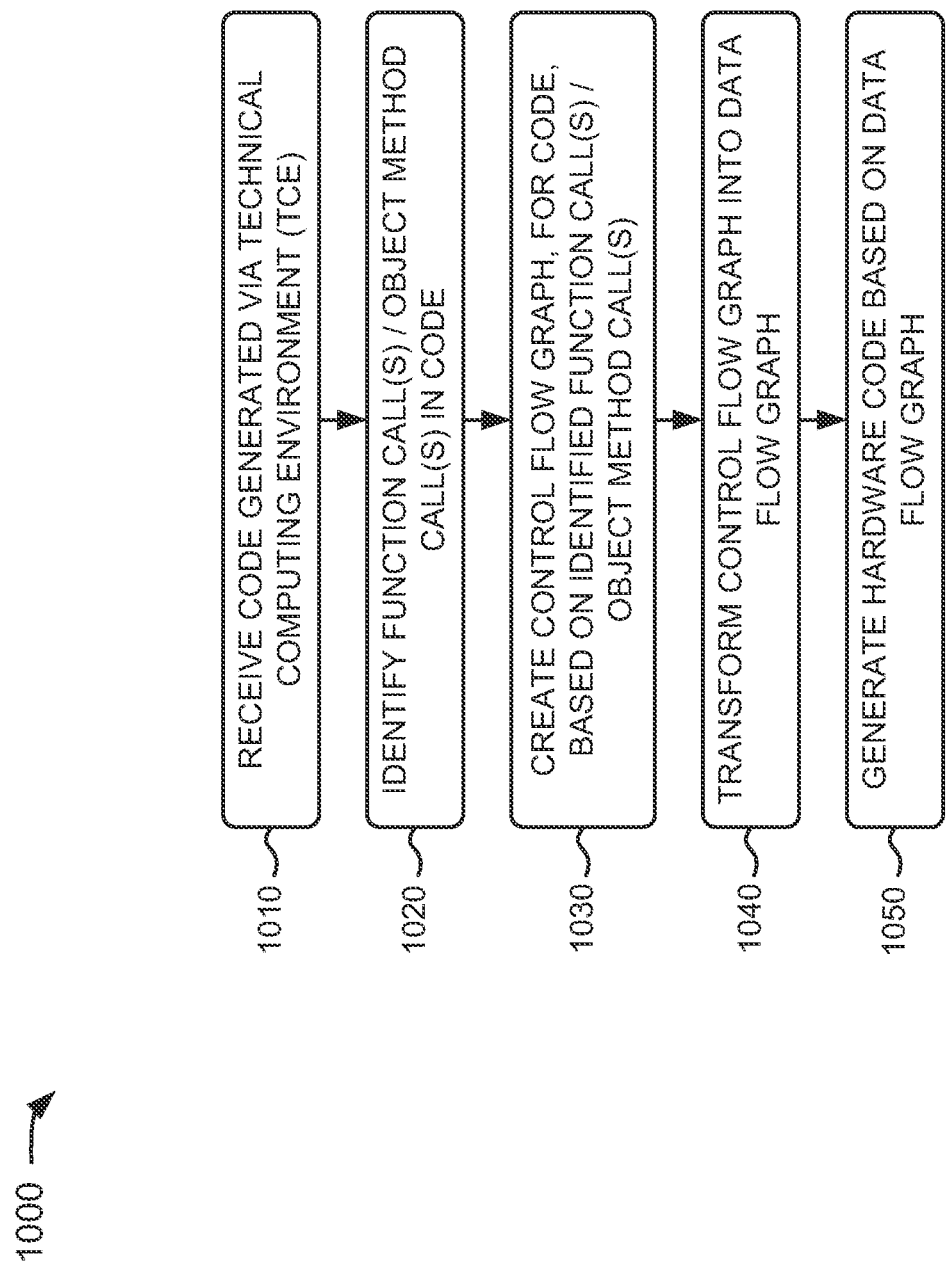
FIGS. 10-12 are flow charts of an example process for identifying function calls and/or object method calls in code generated by a TCE.
Figure 11:
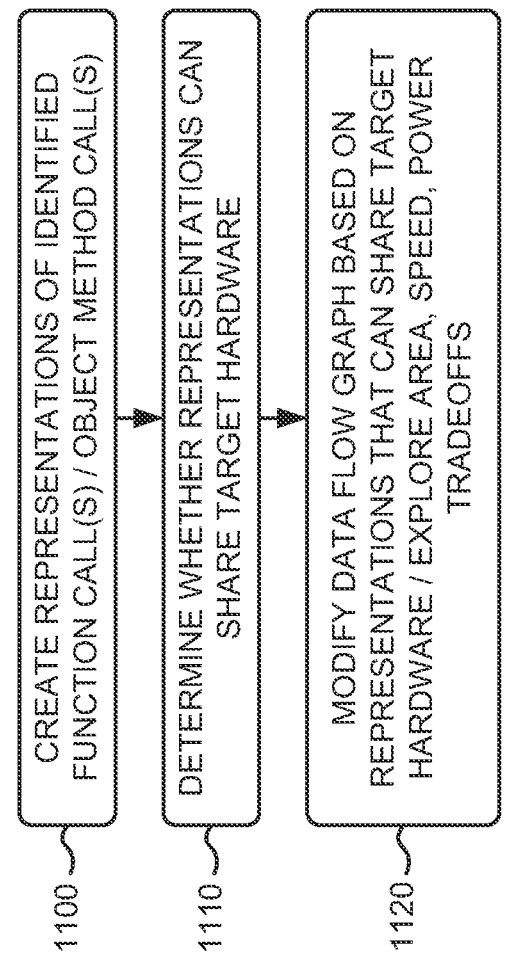
Figure 12:
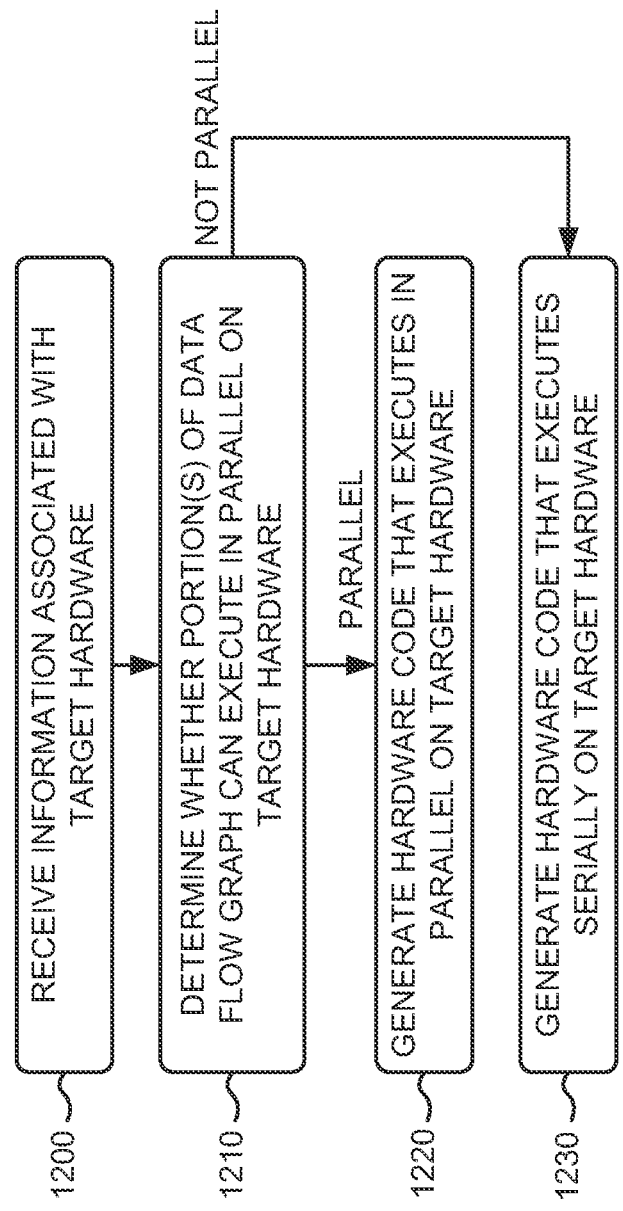

FIGS. 10-12 are flow charts of an example process 1000 for identifying function calls and/or object method calls in code generated by a TCE. In one implementation, process 1000 may be performed by client device 210/TCE 240. Alternatively, or additionally, process 1000 may be performed by another device or a group of devices separate from or including client device 210/TCE 240.

As shown in FIG. 10, process 1000 may include receiving code generated via a technical computing environment (TCE) (block 1010), and identifying function call(s) and/or object method call(s) in the code (block 1020). For example, in an implementation described above in connection with FIG. 5, code identifier component 510 of TCE 240 may receive code 530 generated by TCE 240. TCE code 530 may include text-based code that may require further processing to execute, binary code that may be executed, text files that may be executed in conjunction with other executables, etc. Code identifier component 510 may identify one or more function calls and/or object method calls in TCE code 530, as indicated by reference number 540. In one example, code identifier component 510 may use data types, sizes, complexity, etc. information associated with TCE code 530 to infer or identify a hierarchy of function calls/object method calls 540 in TCE code 530.

As further shown in FIG. 10, process 1000 may include generating a control flow graph, for the code, based on the identified function call(s) and/or object method call(s) (block 1030). For example, in an implementation described above in connection with FIG. 5, code identifier component 510 may create a control flow graph, for TCE code 530, based on the identified function calls and/or object method calls 540. The control flow graph may preserve the hierarchy of the identified function calls and/or object method calls 540.

Returning to FIG. 10, process 1000 may include transforming the control flow graph into a data flow graph (block 1040), and generating hardware code based on the data flow graph (block 1050). For example, in an implementation described above in connection with FIG. 5, code identifier component may transform the control flow graph into a data flow graph 550. Data flow graph 550 may include nodes and/or signals provided between the nodes. The nodes may include representations of function calls/object method calls 540 that are to be executed by one or more hardware devices of an architecture model. The signals may include representations of connections provided between function calls/object method calls 540. Code identifier component 510 may provide data flow graph 550 to hardware code generator component 520 of TCE 240. Hardware code generator component 520 may receive data flow graph 550, and may receive target hardware information 560. Hardware code generator component 520 may generate optimized hardware code 570 based on data flow graph 550 and target hardware information 560.

Process block 1040 may include the process blocks depicted in FIG. 11. As shown in FIG. 11, process block 1040 may include creating representations of the identified function call(s) and/or object method call(s) (block 1100), determining whether the representations can share target hardware (block 1110), and modifying the data flow graph based on the representations that can share target hardware and/or explore area, speed, and/or power tradeoffs for the target hardware (block 1120). For example, in an implementation described above in connection with FIG. 6, data flow graph 640 may include representations 650 of function calls 620 that are to be executed by one or more hardware devices of an architecture model. In one example, data flow graph 640 may include a first representation 650 (e.g., a node labeled "LCP") for a first function call 620 (e.g., t1=leftchannel-processing(u)), and a second representation 650 (e.g., a node labeled "RCP") for a second function call 620 (e.g., t2=rightchannel-processing (u)). In one example, TCE 240 may determine that function calls 620 (e.g., t1=leftchannel-processing(u) and t2=rightchannel-processing(u)) are identical and require the same hardware devices. TCE 240 may configure hardware code 670 to utilize single hardware device 680 (e.g., rather than two separate hardware devices) for function calls 620. The two representations 650 (e.g., the LCP node and the RCP node) for function calls 620 may be merged into a single representation (e.g., a node labeled "LCP/RCP") that may be executed on single hardware device 680.

Process block 1050 may include the process blocks depicted in FIG. 12. As shown in FIG. 12, process block 1050 may include receiving information associated with target hardware (block 1200), and determining whether portion(s) of the data flow graph can execute in parallel on the target hardware (block 1210). For example, in an implementation described above in connection with FIG. 5, hardware code generator component 520 may receive data flow graph 550, and may receive target hardware information 560 (e.g., from a user of TCE 240). Target hardware information 560 may include information associated with hardware devices (e.g., of the architecture model) upon which TCE code 530 is to be executed.

As further shown in FIG. 12, if portion(s) of the data flow graph can execute in parallel (block 1210—PARALLEL), process block 1050 may include generating hardware code that executes in parallel on the target hardware (block 1220). If portion(s) of the data flow graph cannot execute in parallel (block 1210—NOT PARALLEL), process block 1050 may include generating hardware code that executes serially on the target hardware (block 1230). For example, in an implementation described above in connection with FIG. 5, hardware code generator component 520 may generate optimized hardware code 570 based on data flow graph 550 and target hardware information 560. In one example, hardware code generator component 520 may determine that TCE code 530 includes function calls/object method calls 540 that may be executed in parallel. Hardware code generator component 520 may configure hardware code 570 to execute such function calls/object method calls 540 in parallel, which may conserve execution time of hardware code 570. Alternatively, if TCE code 530 includes function calls/object method calls 540 that may not be executed in parallel, hardware code generator component 520 may configure hardware code 570 to serially execute such function calls/object method calls 540.

CONCLUSION

Systems and/or methods described herein may identify function calls and/or object method calls in TCE designs targeted for hardware code generation. In one example, the systems and/or methods may receive code generated by a TCE, and may identify function call(s) and/or object method call(s) in the code. The systems and/or methods may create a control flow graph, for the code, based on the identified function call(s) and/or object method call(s). The control flow graph may preserve the hierarchy of the identified function call(s) and/or object method call(s). The systems and/or methods may transform the control flow graph into a data flow graph, and may generate hardware code based on the data flow graph. The data flow graph may be analyzed to determine opportunities for numeric and latency optimization in the code. Such opportunities may be implemented in the hardware code.

The foregoing description of implementations provides illustration and description, but is not intended to be exhaustive or to limit the implementations to the precise form disclosed. Modifications and variations are possible in light of the above teachings or may be acquired from practice of the implementations.

For example, while series of blocks have been described with regard to FIGS. 10-12, the order of the blocks may be modified in other implementations. Further, non-dependent blocks may be performed in parallel.

It will be apparent that example aspects, as described above, may be implemented in many different forms of software, firmware, and hardware in the implementations illustrated in the figures. The actual software code or specialized control hardware used to implement these aspects should not be construed as limiting. Thus, the operation and behavior of the aspects were described without reference to the specific software code—it being understood that software and control hardware could be designed to implement the aspects based on the description herein.

Further, certain portions of the implementations may be implemented as a "component" that performs one or more functions. This component may include hardware, such as a processor, an application-specific integrated circuit (ASIC), or a field-programmable gate array (FPGA), or a combination of hardware and software.

Even though particular combinations of features are recited in the claims and/or disclosed in the specification, these combinations are not intended to limit the disclosure of the specification. In fact, many of these features may be combined in ways not specifically recited in the claims and/or disclosed in the specification. Although each dependent claim listed below may directly depend on only one other claim, the disclosure of the specification includes each dependent claim in combination with every other claim in the claim set.

No element, act, or instruction used in the present application should be construed as critical or essential unless explicitly described as such. Also, as used herein, the article "a" is intended to include one or more items. Where only one item is intended, the term "one" or similar language is used. Further, the phrase "based on" is intended to mean "based, at least in part, on" unless explicitly stated otherwise.

What is claimed is:

1. A device comprising:
one or more processors to:
receive program code generated via a technical computing environment (TCE),
the program code including code that requires further processing to execute,
identify one or more function calls or one or more object method calls in the program code,
create a control flow graph, for the program code, based on the one or more function calls or the one or more object method calls,
transform the control flow graph into a data flow graph, the data flow graph including a representation for each of the one or more function calls or a representation for each of the one or more object method calls,
receive information associated with a target hardware device, and
generate hardware code for execution on the target hardware device based on the data flow graph and the information associated with the target hardware device,
the hardware code including code that does not require further processing to execute,
when generating the hardware code, the one or more processors are further to
generate two or more portions of the hardware code to execute in parallel on the target hardware device when:
one or more of the representation for each of the one or more function calls can execute in parallel on the target hardware device, or
one or more of the representation for each of the one or more object method calls can execute in parallel on the target hardware device.

2. The device of claim 1, where, when transforming the control flow graph into the data flow graph, the one or more processors are further to:
create the representation for each of the one or more function calls or the representation for each of the one or more object method calls,
determine that one or more representations, of the representation for each of the one or more function calls or the representation for each of the one or more object method calls, can share the target hardware device during execution, and
modify the data flow graph based on determining that the one or more representations can share the target hardware device during execution.

3. The device of claim 1, where, when generating the hardware code, the one or more processors are further to:
determine that one or more representations, of the representation for each of the one or more function calls or the representation for each of the one or more object method calls, can execute in parallel on the target hardware device, and
generate portions of the hardware code to execute in parallel on the target Hardware device based on determining that the one or more representations can execute in parallel on the target hardware device.

4. The device of claim 1, where, when generating the hardware code, the one or more processors are further to:
determine that one or more representations, of the representation for each of the one or More function calls or the representation for each of the one or more object method calls, cannot execute in parallel on the target hardware device, and
generate the hardware code to serially execute on the target hardware device based on determining that the one or more representations cannot execute in parallel on the target hardware device.

5. The device of claim 1, where the hardware code includes text-based code that does not require further processing to execute.

6. The device of claim 1, where the hardware code includes one or more of: C++ code, Hardware Description Language (HDL) code, very-high-speed integrated circuits (VHSIC) HDL(VHDL) code, Verilog code, or Java code.

7. A method, comprising:
receiving program code generated via a technical computing environment (TCE),
the program code including code that requires further processing to execute and the receiving being performed by one or more devices;
identifying one or more function calls or one or more object method calls in the program code,
the identifying being performed by the one or more devices;
creating a control flow graph, for the program code, based on the one or more function calls or the one or more object method calls,
the creating being performed by the one or more devices;
transforming the control flow graph into a data flow graph,
the data flow graph including a representation for each of the one or more function calls or the one or more object method calls,
the transforming being performed by the one or more devices;
receiving information associated with a target hardware device, the receiving the information associated with the target hardware device being performed by the one or more devices; and generating hardware code based on the data flow graph and the information associated with the target hardware device, the hardware code including code that does not require further processing to execute, the generating the hardware code being performed by the one or more devices, the generating the hardware code comprising:

generating one or more portions of the hardware code to execute in parallel on the target hardware device when one or more representations, of the representation for each of the one or more function calls or the one or more object method calls, can execute in parallel on the target hardware device.

8. A method, comprising:

receiving program code generated via a technical computing environment (TCE), the program code including code that requires further processing to execute, and the receiving being performed by one or more devices;

identifying one or more function calls or one or more object method calls in the program code, the identifying being performed by the one or more devices;

creating a control flow graph, for the program code, based on the one or more function calls or the one or more object method calls, the creating being performed by the one or more devices;

transforming the control flow graph into a data flow graph, the data flow graph including a representation for each of the one or more function calls or a representation for each of the one or more object method calls, the transforming being performed by the one or more devices;

receiving information associated with a target hardware device, the receiving the information associated with the target hardware device being performed by the one or more devices; and generating hardware code based on the data flow graph and the information associated with the target hardware device, the hardware code including code that does not require further processing to execute, the generating the hardware code being performed by the one or more devices, the generating the hardware code comprising:

generating two or more portions of the hardware code to execute in parallel on the target hardware device when:

one or more representations, of the representation for each of the one or more function calls, can execute in parallel on the target hardware device, or one or more representations, of the representation for each of the one or more object method calls, can execute in parallel on the target hardware device.

9. The method of claim 8, where transforming the control flow graph into the data flow graph further comprises:

creating the representation for each of the one or more function calls or the representation for each of the one or more object method calls;

determining that one or more representations, of the representation for each of the one or more function calls or the representation for each of the one or more object method calls, can share the target hardware device during execution; and modifying the data flow graph based on determining that the one or more representations, of the representation for each of the one or more function calls or the representation for each of the one or more object method calls, can share the target hardware device during execution.

10. The method of claim 8, where generating the hardware code further comprises:

determining that one or more representations, of the representation for each of the one or more function calls or the representation for each of the one or more object method calls, can execute in parallel on the target hardware device; and generating portions of the hardware code to execute in parallel on the target hardware device based on determining that the one or more representations, of the representation for each of the one or more function calls or the representation for each of the one or more object method calls, can execute in parallel on the target hardware device.

11. The method of claim 8, where generating the hardware code further comprises:

determining that one or more representations, of the representation for each of the one or more function calls or the representation for each of the one or more object method calls, cannot execute in parallel on the target hardware device; and generating the hardware code to serially execute on the target hardware device based on determining that the one or more representations, of the representation for each of the one or more function calls or the representation for each of the one or more object method calls, cannot execute in parallel on the target hardware device.

12. The method of claim 7, where the hardware code includes one or more of: C++ code, Hardware Description Language (HDL) code, very-high-speed integrated circuits (VHSIC) HDL(VHDL) code, Verilog code, or Java code.

13. One or more non-transitory computer-readable media storing instructions, the instructions comprising:

one or more instructions that, when executed by a processor of a device, cause the processor to:

receive program code generated via a technical computing environment (TCE), the program code including code that requires further processing to execute, identify one or more function calls or one or more object method calls in the program code, each of the one or more function calls including a function name followed by one or more arguments, each of the one or more object method calls including function syntax that passes an object as a first argument, create a control flow graph, for the program code, based on the one or more function calls or the one or more object method calls, transform the control flow graph into a data flow graph, the data flow graph including a representation for each of the one or more function calls or the one or more object method calls, receive information associated with a target hardware device, and generate hardware code based on the data flow graph and the information associated with the target hardware device, the hardware code including code that does not require further processing to execute, the one or more instructions to generate the hardware code including:

one or more instructions to determine whether one or more representations, of the representation for each of the one or more function calls or the one or more object method calls, can execute in parallel on the target hardware device, and one or more instructions to generate one or more portions of the hardware code to execute in parallel on the target hardware device when the one or more representations can execute in parallel on the target hardware device.

14. The one or more non-transitory computer-readable media of claim 13, the instructions further comprising: one or more instructions that, when executed by the processor, cause the processor to: create the representation for each of the one or more function calls or the one or more object method calls, determine that one or more representations, of the representation for each of the one or more function calls or the one or more object method calls, can share the target hardware device during execution, and modify the data flow graph based on determining that the one or more representations can share the target hardware device during execution.

15. One or more non-transitory computer-readable media storing instructions, the instructions comprising:

one or more instructions that, when executed by a processor of a device, cause the processor to:

receive program code generated via a technical computing environment (TCE), the program code including code that requires further processing to execute, identify one or more function calls or one or more object method calls in the program code, each of the one or more function calls including a function name followed by one or more arguments, each of the one or more object method calls including function syntax that passes an object as a first argument, create a control flow graph, for the program code, based on the one or more function calls or the one or more object method calls, transform the control flow graph into a data flow graph, the data flow graph including a representation for each of the one or more function calls or a representation for each of the one or more object method calls, receive information associated with a target hardware device, and generate hardware code based on the data flow graph and the information associated with the target hardware device, the hardware code including code that does not require further processing to execute, the one or more instructions to generate the hardware code including:

one or more instructions to determine whether one or more representations, of the representation for each of the one or more function calls or the representation for each of the one or more object method calls, can execute in parallel on the target hardware device, and one or more instructions to generate two or more portions of the hardware code to execute in parallel on the target hardware device when the one or more representations can execute in parallel on the target hardware device.

16. The one or more non-transitory computer-readable media of claim 15, the instructions further comprising:

one or more instructions that, when executed by the processor, cause the processor to:

create the representation for each of the one or more function calls or the representation for each of the one or more object method calls, determine that the one or more representations, of the representation for each of the one or more function calls or the representation for each of the one or more object method calls, can share the target hardware device during execution, and modify the data flow graph based on determining that the one or more representations can share the target hardware device during execution.

17. The one or more non-transitory computer-readable media of claim 15, the instructions further comprising:

one or more instructions that, when executed by the processor, cause the processor to:

determine that the one or more representations, of the representation for each of the one or more function calls or the representation for each of the one or more object method calls, can execute in parallel on the target hardware device, and generate the two or more portions of the hardware code to execute in parallel on the target hardware device based on determining that the one or more representations can execute in parallel on the target hardware device.

18. The one or more non-transitory computer-readable media of claim 15, the instructions further comprising:

one or more instructions that, when executed by the processor, cause the processor to:

determine that the one or more representations, of the representation for each of the one or more function calls or the one or more object method calls, cannot execute in parallel on the target hardware device, and generate the hardware code to serially execute on the target hardware device based on determining that the one or more representations cannot execute in parallel on the target hardware device.

19. The one or more non-transitory computer-readable media of claim 15, where the program code includes one or more of: a text-based code that requires further processing to execute, an executable binary code, text files that execute in conjunction with other executables, or a dynamically-typed programming code.

20. The one or more non-transitory computer-readable media of claim 15, where the hardware code includes text-based code that does not require further processing to execute.

* * * * *

UNITED STATES PATENT AND TRADEMARK OFFICE
CERTIFICATE OF CORRECTION

| | | |
|---|---|---|
| PATENT NO. | : 9,032,380 B1 | Page 1 of 2 |
| APPLICATION NO. | : 13/693439 | |
| DATED | : May 12, 2015 | |
| INVENTOR(S) | : Ruthramoorthy et al. | |

It is certified that error appears in the above-identified patent and that said Letters Patent is hereby corrected as shown below:

Please correct claim 4 as follows:

Column 20, line 29, should read "for each of the one or more function calls or the"

Please replace claim 7 with the following:

"7. The device of claim 1, where the program code includes one or more of:
a text-based code that requires further processing to execute,
an executable binary code,
text files that execute in conjunction with other executables, or
a dynamically-typed programming code."

Please replace claims 12-14 with the following:

"12. The method of claim 8, where the program code includes one or more of:
a text-based code that requires further processing to execute,
an executable binary code,
text files that execute in conjunction with other executables, or
a dynamically-typed programming code.

13. The method of claim 8, where the hardware code includes text-based code that does not require further processing to execute.

Signed and Sealed this
Seventh Day of June, 2016

Michelle K. Lee
*Director of the United States Patent and Trademark Office*

14. The method of claim 8, where the hardware code includes one or more of:
C++ code,
Hardware Description Language (HDL) code,
very-high-speed integrated circuits (VHSIC) HDL(VHDL) code, Verilog code, or Java code."